(12) United States Patent
Swift et al.

(10) Patent No.: US 10,080,697 B2
(45) Date of Patent: Sep. 25, 2018

(54) MOTION SYSTEM WITH PLURALITY OF STEWART PLATFORM BASED ACTUATORS

(71) Applicant: SOC Robotics Inc., North Vancouver (CA)

(72) Inventors: Stephen Glen Swift, North Vancouver (CA); Michael Peter McCrodan, Fort Langley (CA); Siamak Arzanpour, Port Coquitlam (CA); Sohell Sadeqi, Vancouver (CA)

(*) Notice: Subject to any disclaimer, the term of this patent is extended or adjusted under 35 U.S.C. 154(b) by 230 days.

(21) Appl. No.: 14/751,004

(22) Filed: Jun. 25, 2015

(65) Prior Publication Data

US 2016/0016309 A1    Jan. 21, 2016

Related U.S. Application Data

(60) Provisional application No. 62/024,523, filed on Jul. 15, 2014.

(51) Int. Cl.
| | |
|---|---|
| *A61F 2/50* | (2006.01) |
| *A61H 3/00* | (2006.01) |
| *B25J 9/00* | (2006.01) |
| *A61H 1/02* | (2006.01) |
| *A61B 34/30* | (2016.01) |

(52) U.S. Cl.
CPC ............. *A61H 3/00* (2013.01); *A61H 1/024* (2013.01); *A61H 1/0244* (2013.01); *A61H 1/0266* (2013.01); *B25J 9/0006* (2013.01); *B25J 9/0069* (2013.01); *B25J 9/0075* (2013.01); *A61B 2034/304* (2016.02); *A61H 2201/0165* (2013.01); *A61H 2201/0192* (2013.01); *A61H 2201/123* (2013.01); *A61H 2201/1215* (2013.01); *A61H 2201/1246* (2013.01); *A61H 2201/164* (2013.01); *A61H 2201/165* (2013.01); *A61H 2201/1628* (2013.01); *A61H 2201/5007* (2013.01); *A61H 2201/5061* (2013.01); *A61H 2201/5064* (2013.01); *A61H 2201/5094* (2013.01); *A61H 2230/60* (2013.01); *G05B 2219/50162* (2013.01); *G05B 2219/50169* (2013.01)

(58) Field of Classification Search
CPC ...... A61F 2/48; A61F 2/50; A61F 2/72; A61F 2002/5003; A61F 2002/5033
See application file for complete search history.

(56) References Cited

U.S. PATENT DOCUMENTS

| | | | | |
|---|---|---|---|---|
| 2007/0191743 A1* | 8/2007 | McBean | ............ | A61B 5/04888 601/5 |
| 2009/0276058 A1* | 11/2009 | Ueda | .................... | A61H 1/0274 623/57 |
| 2011/0082566 A1* | 4/2011 | Herr | ......................... | A61F 2/60 623/24 |

\* cited by examiner

*Primary Examiner* — Bruce E Snow

(57) ABSTRACT

Examples of a motion system are disclosed. The motion system comprises a plurality of Stewart platform based actuators connected one to each another forming a desired modular configuration. Each of the plurality of actuators is controlled by a central controller that is configured to independently control the plurality actuators and adjust in real time their position, orientation and motion trajectory. The plurality of actuators are arranged in the desired configuration, shape and size to provide motion system that can mimic a natural motion/gait of human or animal body.

26 Claims, 7 Drawing Sheets

MOTION SYSTEM WITH PLURALITY OF STEWART PLATFORM BASED ACTUATORS

This application claims priority from the U.S. Provisional Patent Application No. 62/024,523, filed Jul. 15, 2014.

BACKGROUND OF THE INVENTION

Technical Field

The present disclosure generally relates to a high performance actuators and more particularly relates to a motion system with Stewart platform based actuators.

Background

Unless otherwise indicated herein, the materials described in this section are not prior art to the claims in this application and are not admitted to be prior art by inclusion in this section.

Linear/rotary hexapod (Stewart platform) actuators can be used to directly mimic a motion of existing industrial (Cartesian) robots and milling machines but have not been used in motion systems that mimic human or animal locomotion. Human and animal locomotion can be influenced by several factors such as neuromuscular and joint disorders which can affect the functionality of joints and can reduce their mobility. Many individuals with limited mobility require mobility assistive technologies to keep up with their daily life. A wearable exoskeleton robot is an external structural mechanism with joints and links corresponding to those of human body that are synchronized with its motion to enhance or support natural body movements. The exoskeleton transmits torques from its actuators through rigid exoskeletal links to the human joints and thereby augments human strength. Currently several lower limb exoskeleton mobility assistive devices are known and available on the market. For example, the devices developed by Argo Medical Technologies Ltd. (ReWalk-I™ and ReWalk-P™); Esko Bionics Inc. (eLEG™); Cyberdyne Inc. (HAL™); Rex Bionix (REX™); University of California at Berkeley (BLEEXD™) can assist with sitting, turning and climbing and descending stairs and slopes. All of these mechanisms are designed as serial manipulators which consist of a number of rigid links connected in serial by the connecting joints which forces each actuator to support the weight of its successor links and results in a low payload-to-weight ratio characteristics with poor force exertion capabilities. The accuracy in positioning the payload and speed of manipulation is another drawback of the known serial robots.

There is a need for a precise and accurate actuators that can be used in mobility assistive devices and/or other robotic applications that overcome the limitations of the known prior art actuators.

SUMMARY

In one aspect, a motion system is provided. The motion system comprises a plurality of Stewart platform based actuators connected one to another forming a desired modular configuration. A system's central controller is in communication with each of the plurality of actuators to independently control the plurality of actuators and to adjust in real time their position, orientation and motion trajectory.

The motion system further comprises a plurality of sensors to capture a position of each of the actuators in real time. The central controller receives an input signal from the plurality of sensors and adjusts a trajectory of each of the actuators in real time based on the received input signal.

In another aspect, the central controller receives an input signal by an operator and adjusts a trajectory of each of the actuators in real time based on the signal received from the user.

In one aspect the motion system comprises a linking element to connect two of the neighboring actuators. The linking element can be rigid or flexible. The linking element can further be a damper. The linking damper comprises a driver and a controller that is in communication with the driver to control and adjust a stiffness of the linking damper and thus stiffness of the motion system.

The motion system further comprises a motion capture unit comprising a plurality of motion sensors and a motion simulation unit in communication with the motion capturing unit and the central controller. The motion simulating unit is configured to receive signals provided by the motion capturing unit, then process such signals and provide output signals to the central controller to actuate the actuators to mimic the motion captured by the motion sensors.

In one aspect the motion system is used as an exoskeleton mobility assistive device.

In another aspect the motion system is used as a full body robotic structure.

In one aspect a reinforced actuator is provided. The reinforced actuator comprises a Stewart platform with a base plate, an upper plate, a plurality of adjustable legs pivotally connected to the upper plate and the base plate, and a driver in communication to the plurality of legs. The leg's driver is configured to adjust a length, orientation and velocity of each of the plurality of legs. The actuator is reinforced with a damper that is rotatably connected to the upper plate and the base plate of the Stewart platform. The damper comprises a driver that adjusts in real time stiffness of the damper and thus the mobility of the actuator. The actuator further comprises a controller that is in communication with the driver of the legs and the driver of the damper. The controller is configured to calculate a position, orientation and a motion trajectory of the plurality of legs and adjust in real time the length, orientation and the trajectory of the plurality of legs and a stiffness of the damper.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

DETAILED DESCRIPTION OF SPECIFIC EMBODIMENTS

Figure 1B:
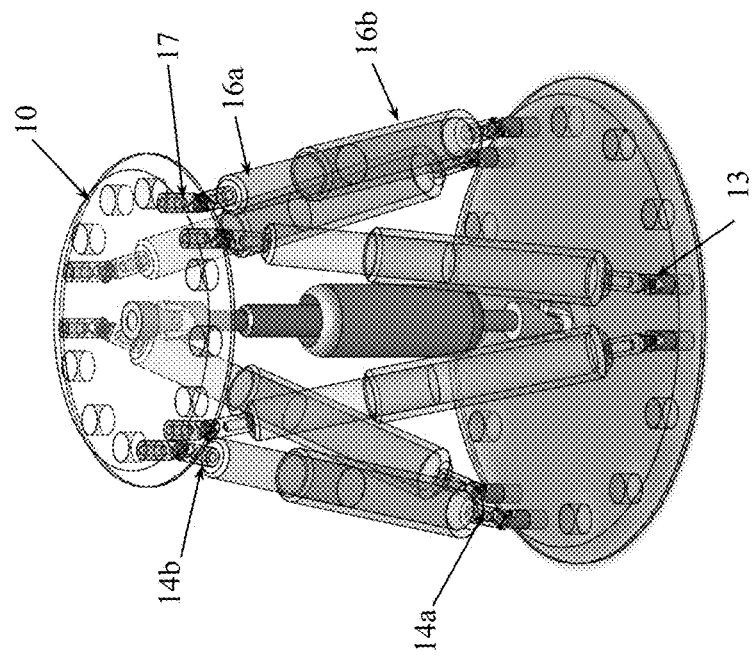
FIGS. 1A and 1B are perspective views of Stewart platform actuator with a damper according to an embodiment of the present invention.

A Stewart platform actuator (also called hexapod) can be used in motion simulators or robotic structures to mimic in a controllable manner certain motions. For example, Stewart platforms can be used in exoskeleton robots to closely reproduce the natural movements/gait of human body. The Stewart platform actuator comprises a body with a top plate connected to a base plate by six individual struts (kinematic legs). Each of these six legs is connected to both plates by universal joints. In this architecture, the load is distributed among several parallel kinematic chains which thereby provide a high nominal load-to-weight ratio with high positioning accuracy and speed. The stress induced in each link is mostly of a traction-compression nature which is quite suitable for linear actuators and therefore contributes to the rigidity of the manipulator.

The Stewart (hexapod) based actuators can be used in motion systems such as, an exoskeleton robot or full body robot to mimic human gait or any other desired movement. For example, such motion system (examples illustrated in FIGS. 5 and 6) can have a modular body having a plurality of Stewart platform actuators stuck to each other and arranged in the desired configuration, shape and size. Each of the actuators is independently control by controlling a length/orientation and speed of each of the legs in the actuators. The actuators can be joined to each other directly or can be connected with a flexible or rigid linking element. In one motion system some of the actuators can be stuck to each other directly while others can be connected with a linking element. For example, FIG. 6 shows a full body robot having a plurality of actuators (e.g. group of actuators indicated with reference number 60) that are connected to each other directly (no linking elements) while some of the actuators (e.g. group of actuators indicated by reference 62) can be connected with linking elements. The actuators in the motion system can be used as joints or bony/muscular structure.

The Stewart platform based actuator can be described with reference to FIGS. 1A and 1B that illustrate an example of the hexapod (Stewart platform with six kinematic legs) based actuator 100. The actuator 100 comprises an upper plate 10 and a base plate 12 that are connected in an articulated manner by a plurality of legs 14. The illustrated example of the actuator 100 is defined as a hexapod which utilizes six kinematic legs 14 that in combination, control a selected position of the upper movable plate 10 within six degrees of freedom relative to the base plate 12 (three translation axes and three rotation axes), at the same time.

Alternate designs can include more than six legs 14 or less than six legs 14 without departing from the scope of the invention. A plurality of connecting joints 13 pivotally attaches the legs 14 to the base 12. For example, the joints 13 can be a U-joint ball receptor formed at an inner surface of the base 12 and a U-joint ball located at a lower end 14a of the leg 14, so that the leg 14 can be pivotally attached to the base 12. Alternatively, the leg 14 can be rotatably attached to the base 12 using any other universal joint such as a single U-joint, a double U-joint, a pin and block U-joint, a needle bearing U-joint or any other known means for rotatably connecting the lower end 14a of the leg 14 to the base 12. The upper plate 10 comprises an inner surface, an outer surface and a plurality of connecting joints 17 (see FIG. 1B) that rotatably connect an upper end 14b of the leg 14 to the upper plate 10. The connecting joints 13 and 17 can be of the same type or different type without departing from the scope of the invention. When used herein, the phrase "rotatably attached", when describing the attachment between two or more parts or elements, means that the referenced parts or elements are attached to one another in such a manner that allows rotation thereinbetween. The base plate 12 can be dimensioned to have a surface area that is greater than, less than or equal to the surface area of the upper plate 10. The actuator 100 can be flipped around so that its upper plate becomes a base plate and vice versa without departing from the scope of the invention as long as there are two plates connected with a plurality of kinematic legs. The upper plate 10 and the base 12 may be constructed in various manners, out of various materials, and in various shapes and sizes. For example, they may consist of one-piece or multiple-pieces.

The legs 14 are positioned between the base plate 12 and the upper plate 10. The legs 14, in combination, control the position of the upper plate 10 within six degrees of freedom relative to the base plate 12 (and vice versa can control the position of the base plate 12 within six degrees of freedom relative to the upper plate 10). Each of the legs 14 is preferably similar in construction to one another. The legs 14 are adjustable (length-wise and orientation-wise) and controllable using a controller 15. Each of the legs 14 can be adjusted (length or orientation) independently by the other legs 14 of the actuator 100. In the example illustrated in FIG. 1B, each of the legs 14 comprises a rod 16a and a tube 16b that is shaped and sized so that the rod 16a can slide partially within the tube 16b. The rod 16a and the tube 16b of the leg 14 are telescopically connected. The length and orientation of each of the legs 14 can be adjusted by sliding or rotating the rod 16a in relation to the tube 16b. The actuator 100 can further comprise six drivers 19 in communication with each of the legs 14 to drive each of the legs 14 in linear or rotational fashion. The driver 19 can be electrical, hydraulic/pneumatic or mechanical driver. Each of the drivers 19 is in communication with the controller 15. FIG. 1A shows only one driver 19 (for clarity only) that is in communication with only one of the legs 14, however the actuator 100 comprises plurality of drivers to drive each of the legs 14 independently from each other. The controller 15 is configured to accurately control length and orientation of each leg 14. The controller 15 can comprise an input/output unit and a processing unit. For example the controller 15 can be a 32 bit system with 6-axis control, 100 BaseT and USB 2.0 interface, 6 quadrature decoding channels and smart limit switch support. The controller 15 can be located remotely from the actuator 100 and can be in communication with the drivers 19 of the legs 14.

In one implementation, the actuator 100 can further comprise a plurality of sensors 23, such as inertial measurement unit (IMU) sensors that can comprise a tri-axial accelerometer, tri-axial rate gyro and tri-axial magnetometer. The sensors measure the position of each of the legs 14 in real time and provide such information to the controller 15 as an input. FIG. 1A shows only one sensor 23 for clarity reasons, however it should be understood that the actuator 100 can comprise a plurality of sensors 23 position at the actuator 100 and/or remotely from it. Based on such input the controller 15 can make calculations of the lengths, orientation and velocities of each of the legs 14 in real time and can provide output signals (step/direction signals) that can be sent to the leg's drivers 19 (e.g. linear axis stepper motor or DC servo motor) to adjust the length and orientation of the legs 14 of the actuator 100. In one implementation, the leg's driver 19 can be any suitable electrical, pneumatic, hydraulic or mechanical driver that can adjust the length, orientation and/or speed of the legs 14 in real time based on the input received from the controller 15. In addition the controller 15 can comprise a signal conditioning circuit. Outputs from the sensors 23 can be processed by the signal conditioning circuit before being processed by the control processing unit. Output from the processing unit is transferred to the power drive to provide the required drive signal (e.g. voltage) to the leg's drivers 19.

In one implementation, the sensors 23 can be omitted and the controller 15 can be designed such that the user can provide inputs that allow changing of the desired conditions or user preferences of motion conditions (flat surfaces, slopes, etc.). In another implementation, such input can be fed into the controller 15 by the sensors 23 and the user. So the controller 15 can receive input from the one or more sensors 23 and/or as user inputs and can provide commands for the leg's drivers 19 based on such input. The sensors 23 can be IMU sensors that can record 3-axis acceleration, 3-axis gyro, 3-axis magnetometer and height (barometric pressure) in real time along with corrected roll, pitch and yaw using a proprietary sensor algorithm. The output of the IMU sensors 23 can be fed directly into the controller 15. The controller 15 can then compare such input data against a predetermined data set (e.g. set up by the user) and can then adjust, if necessary, the output signals transferred to the leg's drivers 19. In one implementation, every leg 14 can comprise a separate microcontroller in communication to the controller 15. In one implementation, only selected legs 14 can be in communication with the controller 15 while the rest are passive or compliant, such as they are manually adjusted but are not motorized or remotely driven.

Figure 1A:
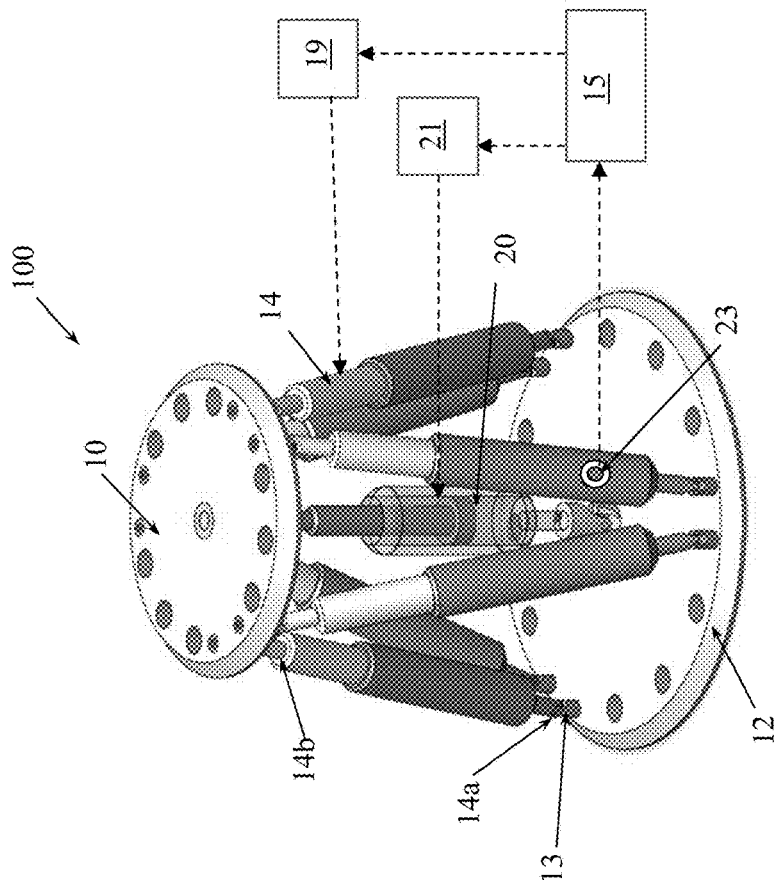

In the example of the actuator 100 illustrated in FIGS. 1A and 1B the actuator 100 is further reinforced with a damper 20. For example, the damper 20 can be positioned between the upper plate 10 and the base 12 and can be configured to adjust the stiffness of the actuator 100. The damper 20 can be configured to increase the payload capacity and can provide high stiffness, speed, and load capability of the actuator 100. In one implementation, the damper 20 can be a Magnetorheological (MR) damper or an Electrorheological (ER) damper or any other suitable damper. A MR damper uses magnetorheological (MR) materials as dry particles or particles dispersed in fluid to provide controllable damping forces. The particles are comprised of magneto-soft particles. For example, the housing of the damper can be filled with suspension of micron-sized magnetizable particles (e.g. iron particles) in an appropriate carrier fluid. The MR fluid is controlled by a magnetic field, usually using an electromagnet. This allows the damping characteristics of the MR damper to be continuously controlled by varying the power of the electromagnet. When the MR fluid is subjected to a magnetic field, the iron particles align along the magnetic lines thus solidifying the suspended iron particles and restricting the fluid movement. The damping force is only dependent on the magnetic field applied to the MR fluid/particles and can be adjusted up to 1,000 times in a second. This means that the MR dampers can respond in real time and can be highly and accurately controllable. The polarizable particles are the basic difference between ER and MR dampers. ER damper uses smaller particles that polarize when directly exposed to an electric current. MR damper uses larger particles that polarize when surrounded by a magnetic field. Any other known suitable damper can be used with the platform 100 to increase its payload capacity and stiffness.

Figure 2B:
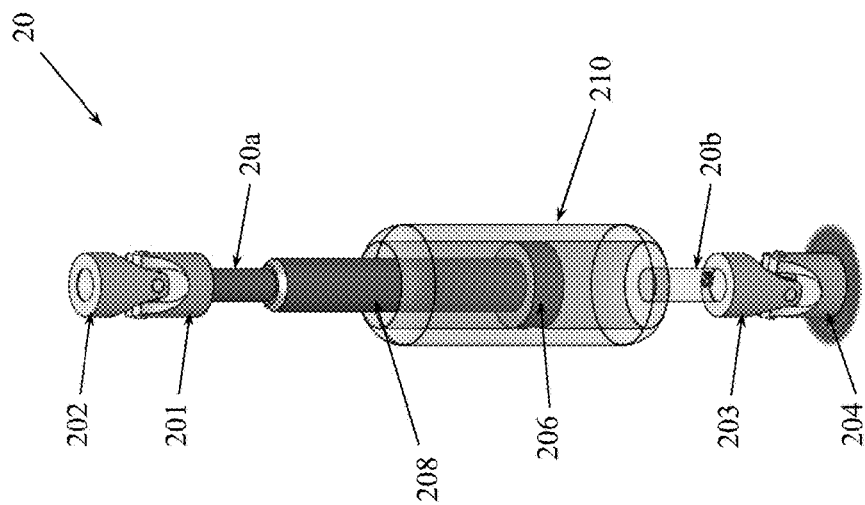
FIG. 2B is a perspective view of the damper of FIG. 2A with a transparent housing to provide view of a movable member.
Figure 2A:
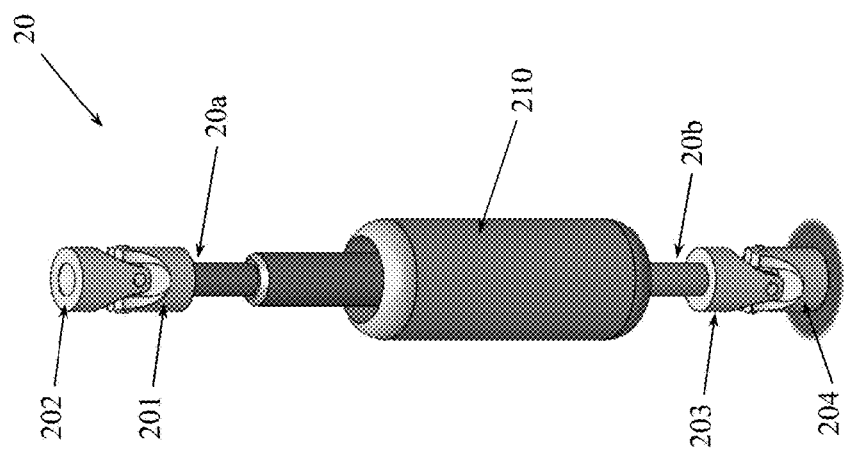
FIG. 2A is a perspective view of an example of a damper for reinforcing an actuator of FIGS. 1A and 1B.

FIGS. 2A and 2B show in details an example of the damper 20. The damper 20 can have an elongated body with a first end 20a configured to be connected to one of the plates of the actuator 100 (e.g. plate 10), and a second end 20b configured to be connected to the opposite plate of the actuator 100 (e.g. base 12). A joint 201 (e.g. a U-joint ball) located at the first end 20a can be used to pivotally attached to a U-joint ball receptor 202 that is attached to the upper plate 10 of the actuator 100. Similarly, a U-joint ball 203 located at the second end 20b can be used to pivotally attached to a U-joint ball receptor 204 that is attached to the base 12 of the actuator 100. Alternatively, the damper 20 can be attached to the upper plate 10 and the base 12 using any other universal joint configured to pivotally attach the damper 20 to the respective plates 10, 12 of the actuator 100. The damper 20 can comprise a housing 210 that contains a magnetically controllable particles/fluid and a movable member 206 (FIG. 2B) mounted for movement through the particles/fluid in the housing 210. In the illustrated example, the movable member 206 is a piston that is connected to the first end 20a of the damper 20 through a rod 208. The housing 210 is hollow having an inner bore with a diameter slightly bigger than an outer diameter of the piston 206 so that the piston 206 and the housing 210 can move in relation to each other in linear or rotatable fashion. The damper 20 can further comprise one or more bearings and seals (not shown) to prevent any fluid leakage out of the housing 210. A small volume of magnetically controllable fluid can be provided in the inner bore of the housing 210. A magnetic field generator 21 (see FIG. 1A) produces a magnetic field for directing the magnetic flux to desired regions of the MR fluid. For example, the magnetic field generator can comprise an electromagnetic coil and a power circuit in communication with the coil to generate magnetic field to increase the stiffness of the damper 20. In one embodiment, the electromagnetic coil can be located inside the piston 206. The rod 208 can be hollow and can be configured to house a power line between the electromagnetic coil and a power source so that when the power source is on, the coil is energized generating a magnetic field. In another embodiment, the electromagnetic coil can be mounted around the housing 210. When the coil is energized by applying a voltage, the fluid in the housing 210 becomes solid thus locking together the piston 206 and the housing 210. By placing the damper 20 between the upper and base plates 10, 12 of the actuator 100, the stiffness of the overall actuator is controllable. The damper 20 can adjust it's length to accommodate the motion of the upper plate 10 with respect to the base plate 12 of the platform 100 meaning that when the power source is turned off and the coil is de-energized the piston 206 can freely move (linearly or in rotational fashion)

in relation to the housing 210 in accordance to the movement of the upper plate 10 and/or the base plate 12. Additionally and alternatively, the damper 20 can be in communication with a controller that can be configured to control the driver of the damper (i.e. magnetic field generator 21) and thus can control the magnetic field and the stiffness of the damper 20 in real time.

Figure 3B:
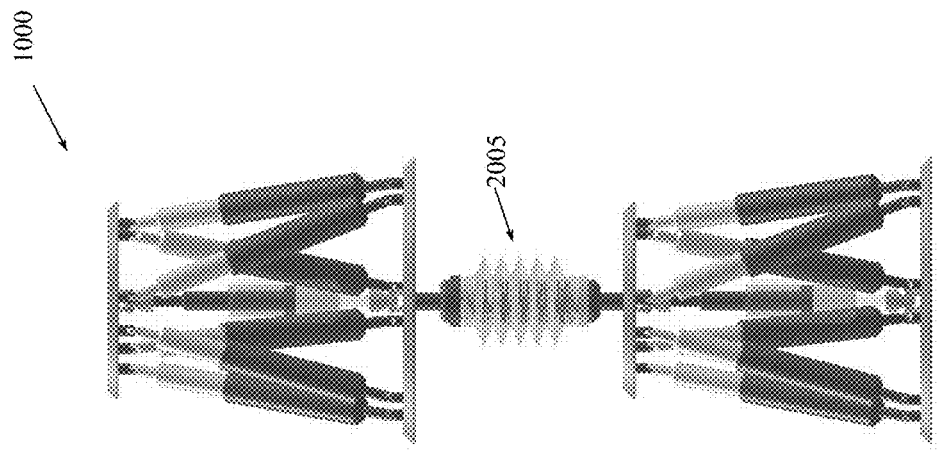
FIG. 3B is a side view of a motion system with two Stewart platform actuators with a damper linking the two actuators.
Figure 3A:
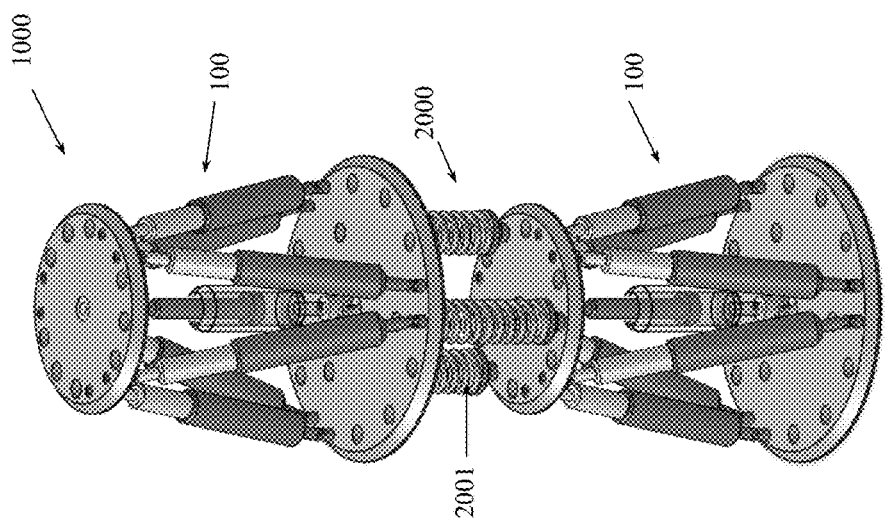
FIG. 3A is a perspective view of a motion system with two Stewart platform actuators with a flexible link between the two actuators.
Figure 4:
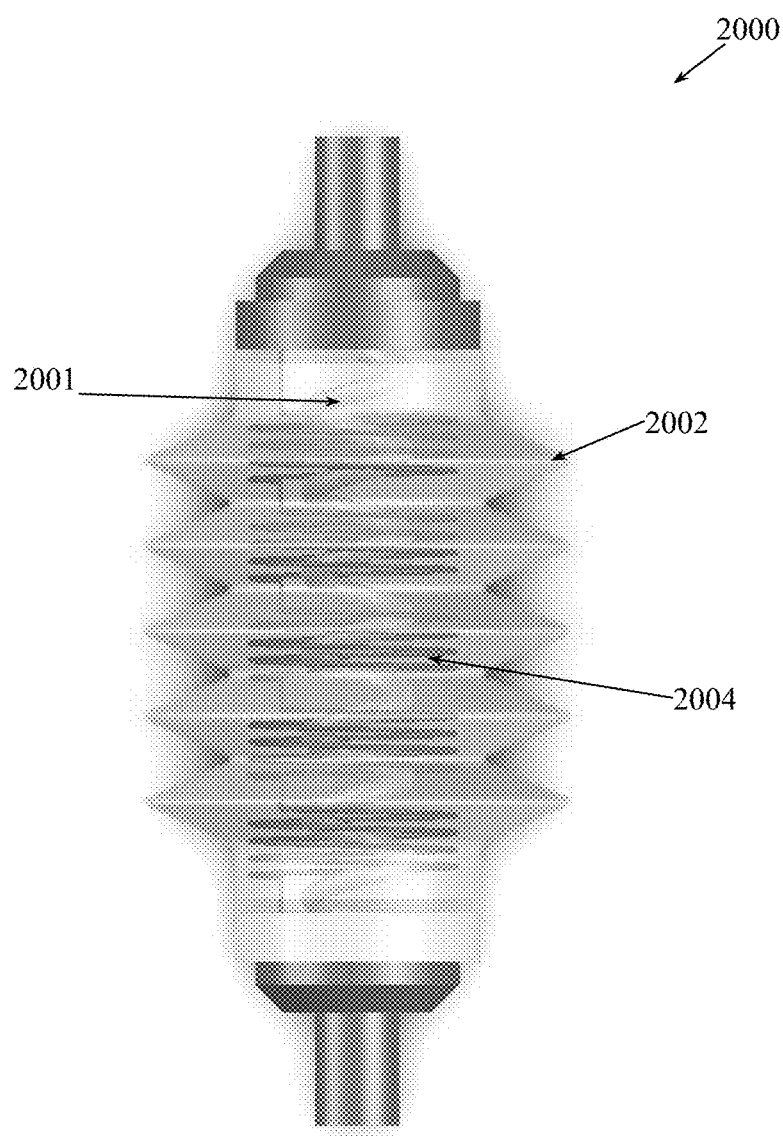
FIG. 4 is a cross-sectional side view of another example of a reinforcing damper of the present invention.

In one implementation, one or more (or all) of the legs 14 can be provided with a housing enclosing at least a portion of the legs 14. A coil can be provided around the housing so that the legs 14 can have a function of a damper when such coil is energized to provide a magnetic field to a MR/ER particles/fluid provided in the housing. The controller that controls the damper 20 can be separate or the same as with the controller 15 of the actuator 100. For example, based on the data fed from the sensors 23 or inputted by the user the controller 15 can send output signals to the leg's drivers 19 and at desired time to the damper's driver 21 to adjust the stiffness (e.g. magnetic field) of the damper 20. Person skilled in the art would understand that the damper 20 can have different configuration than the one illustrated in the FIGS. 2A, 2B without departing from the scope of the invention. For example, FIG. 4 shows an example of a damper in which instead of piston 206 a spring element is utilized. FIGS. 3A and 3B depict a motion system 1000 that comprises at least two Stewart platform based actuators 100. FIGS. 3A and 3B show two actuators 100 connected with a linking element 2000, however the linking element can be omitted and the motion system 1000 can include at least two actuators 100 connected one to another directly with no linking element in between. In the illustrated example at FIG. 3A the linking element is one or more springs 2001 while FIG. 3B shows a linking element that is a damper that is similar to the damper 20 described herein above with reference to FIGS. 2A and 2B. Person skilled in the art would understand that the linking element 2000 connecting any two actuators 100 can be any rigid or flexible element with or without dampening element.

In the example illustrated in FIG. 3A, the link 2000 can be a spring 2001 connecting the two actuators 100. By connecting the two actuators 100 together with the spring 2001 the relative motion of the two actuators 100 with respect to each other can be softened while still preserving a degree of stiffness. In the embodiment illustrated in FIG. 3B, the linking element can been updated to add dampening element to the spring 2001 (becoming a linking damper 2005) by surrounding the spring 2001 with a housing, i.e. a sleeve 2002, that contains MR particles/fluid (see FIG. 4). The sleeve 2002 can be made of any other suitable material and can envelop the spring 2001 in a fluidly tight manner so that no fluid can leak out of the sleeve 2002. In the illustrated example the sleeve 2002 has multiple folds or any other elastic configuration so that its length can be adjusted to accommodate the spring 2001 in its extended and/or retracted position. A coil 2004 (see FIG. 4) can be wrapped around the spring 2001 or the sleeve 2002 and the MR particles/fluid can be inserted in the sleeve 2002, such that the spring's stiffness can be controlled by a voltage applied to the coil 2004. The coil 2004 is in electrical communication with a power supply (not shown). The linking damper 2005 and each of the actuators 100 can be control by the system's central controller (not shown) that independently control and adjust the position/orientation/velocity/stiffness of each of the actuators 100 and the linking damper 2005 in real time to mimic natural or required motion. The adjustable linking dampers 2005 and/or other types of flexible or rigid linking elements 2000 in addition to the actuators 100 can help with the load distribution as well as mimicking the natural flexibility of the body links in extensions and contraction. In one embodiment, each of the actuators 100 in the motion system 1000 and/or each of the linking element/damper can be controlled by a separate microcontroller what are in communication with the central system controller. The high-level commands can be made by the central controller to estimate position of each of the actuators 100 over time while the microcontrollers can be provided to handle low-level calculations required to drive the legs 14 of the actuators 100 for a given desired trajectory which may be time variant.

The motion system 1000 can comprise more than two actuators 100 that can be connected with the linking elements/dampers or can be connected to each other directly with no linking elements in between. In one implementation, the motion system 1000 can comprise plurality of actuators 100 where some of the actuators 100 can be stuck to each other directly while others can be connected with linking elements. Even though the motion system 1000 illustrated in FIGS. 3A and 3B comprises actuators 100 reinforced with damper 20, person skilled in the art would understand that that the actuators 100 can be Stewart platform based actuators with no reinforcing damper 20. In fact, FIGS. 5 and 6 show two examples of a motion system 1000 in which the actuators 100 are without reinforcing damper 20.

Figure 5:
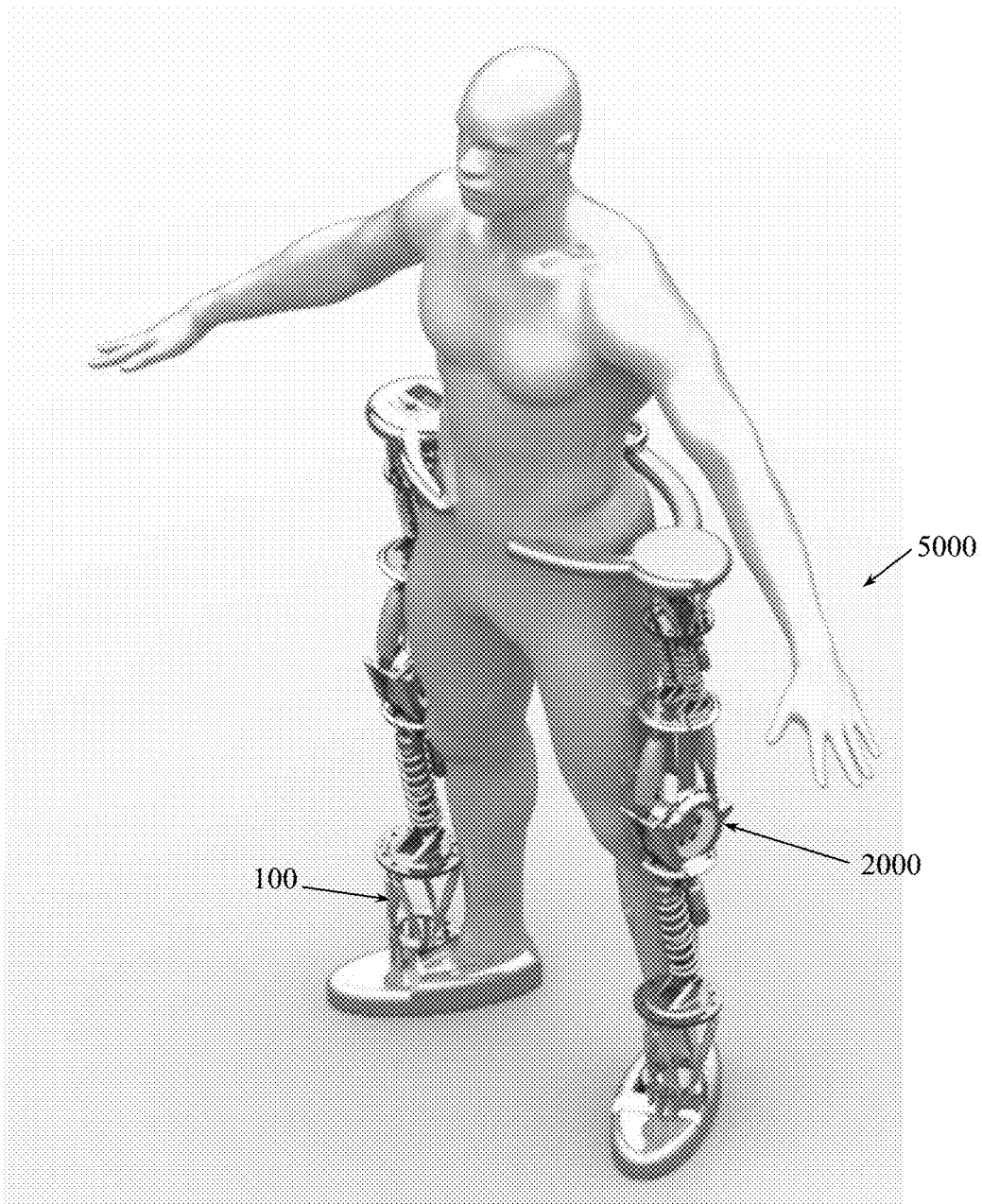
FIG. 5 is a perspective view of an example of a lower limb exoskeleton mobility assistive device of the present invention.
Figure 6:
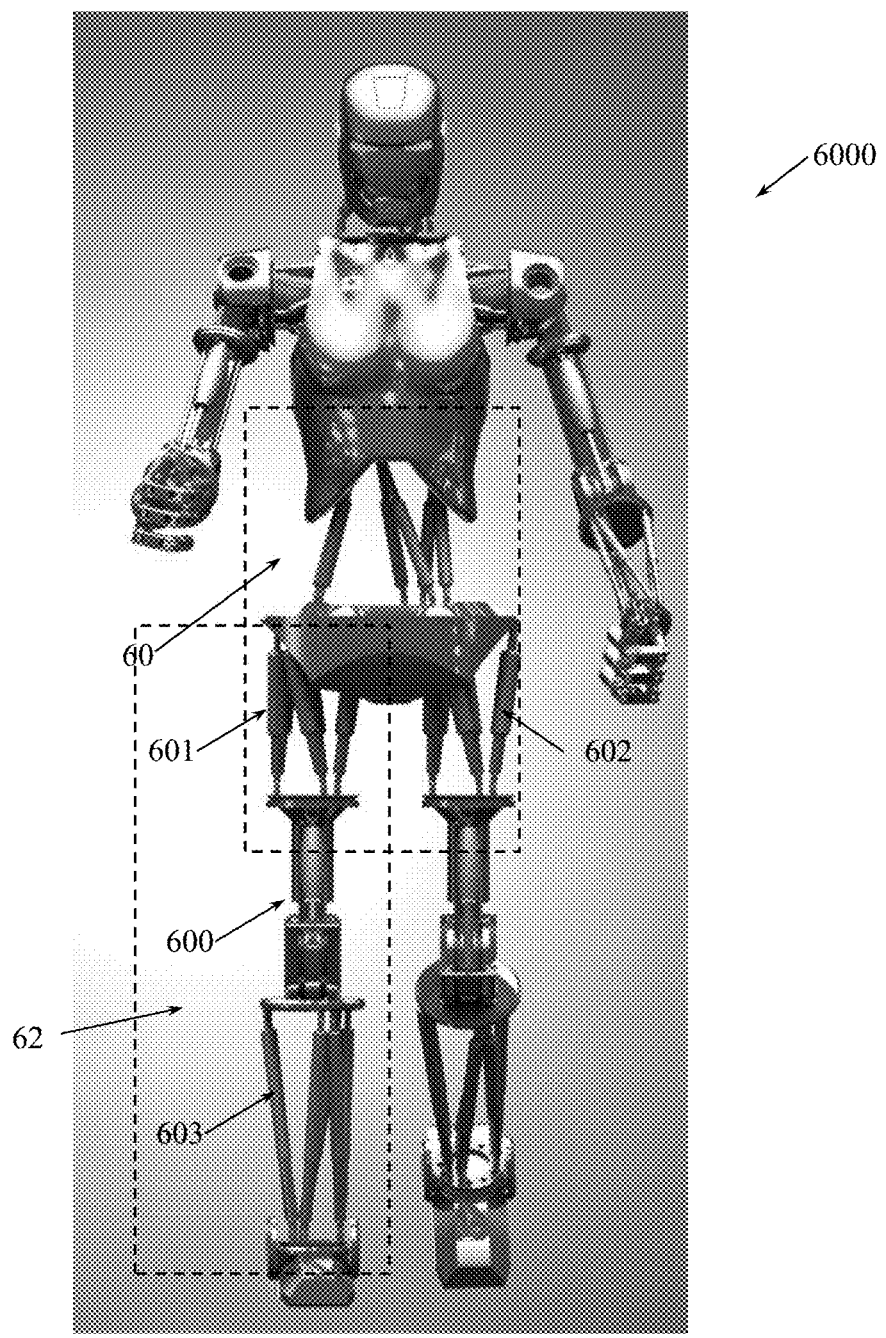
FIG. 6 is a perspective view of an example of a full body robot made with a Stewart platform based actuators.

FIG. 5 shows a motion system 5000 that is a lower limb exoskeleton mobility assistive device with four actuators 100 connected with linking elements 2000. The linking elements can be rigid bars or flexible springs or a combination thereof. In some embodiments some or all of the linking elements can be a damper as the one described with reference to FIGS. 2-4. The advantage of using actuators 100 in human exoskeletal suits is that the actuators 100 have a high strength and can change the length/stiffness thereby reducing pressure points. Such exoskeletal suit is anti-chafing and can change the length during usage. For example, such exoskeletal suit can change the length depending on the performed motion by changing the length and/or orientation of the legs 14 of the actuators 100. Additionally and alternatively, the motion system 5000 can have a high adjustability of the structure design to accommodate different wearers by adjusting the length and design of the actuators 100 and the linking elements 2000.

In one possible application, the system 1000 can be used in a full body hexapod based robot—hexosapian 6000, an example of which is illustrated in FIG. 6. As shown in FIGS. 5 and 6 the multiple actuators 100 can act as joints (e.g. hip, knee, ankle) or skeletal/muscular structure. Some of the actuators 100 in such motion systems can be linked with adjustable flexible links or rigid links or linking dampers (e.g. linking element 600), while some of the actuators 100 can be connected directly with no linking elements in between. For example FIG. 6 shows the full body robot 6000 in which at least one group of three actuators 60 is connected with no linking elements in between. The group 60 comprises three actuators that are connected together directly with no linking elements. The upper plate of the actuators 601 and 602 is adapted to act as a common upper plate for the both actuators. As illustrated in FIG. 6, some of the actuators in the same motion system 6000 can be connected with linking element (e.g. group of actuators 62 comprising actuators 601 and 603 connected with the linking element 600).

The damper's controlling unit can be the same or separate unit and can be incorporated in the actuator's controller 15 or system's central controller. In one implementation, the system's central controller can comprise IMU sensors that can estimate necessary parameters, i.e. segmental orientations, positions and forces of the actuators 100 and/or the connecting elements/dampers 2000, 2005. The central controller can be capable of computing accurately the orientation estimations by fusing raw signals obtained from the sensors (i.e. signals obtained from a tri-axial accelerometer, tri-axial rate gyro and tri-axial magnetometer) accurately calculating the lengths and velocities of each of the legs 14 in each of the actuators 100 of the motion system 1000 and convert such signals into step/direction signals that can be sent to the leg's drivers 19. In one implementation, the central controller can receive the input data from a user/operator. By employing IMU sensors the balance stability of the system 1000 can be quantified and potential falls can be detected.

Figure 7:
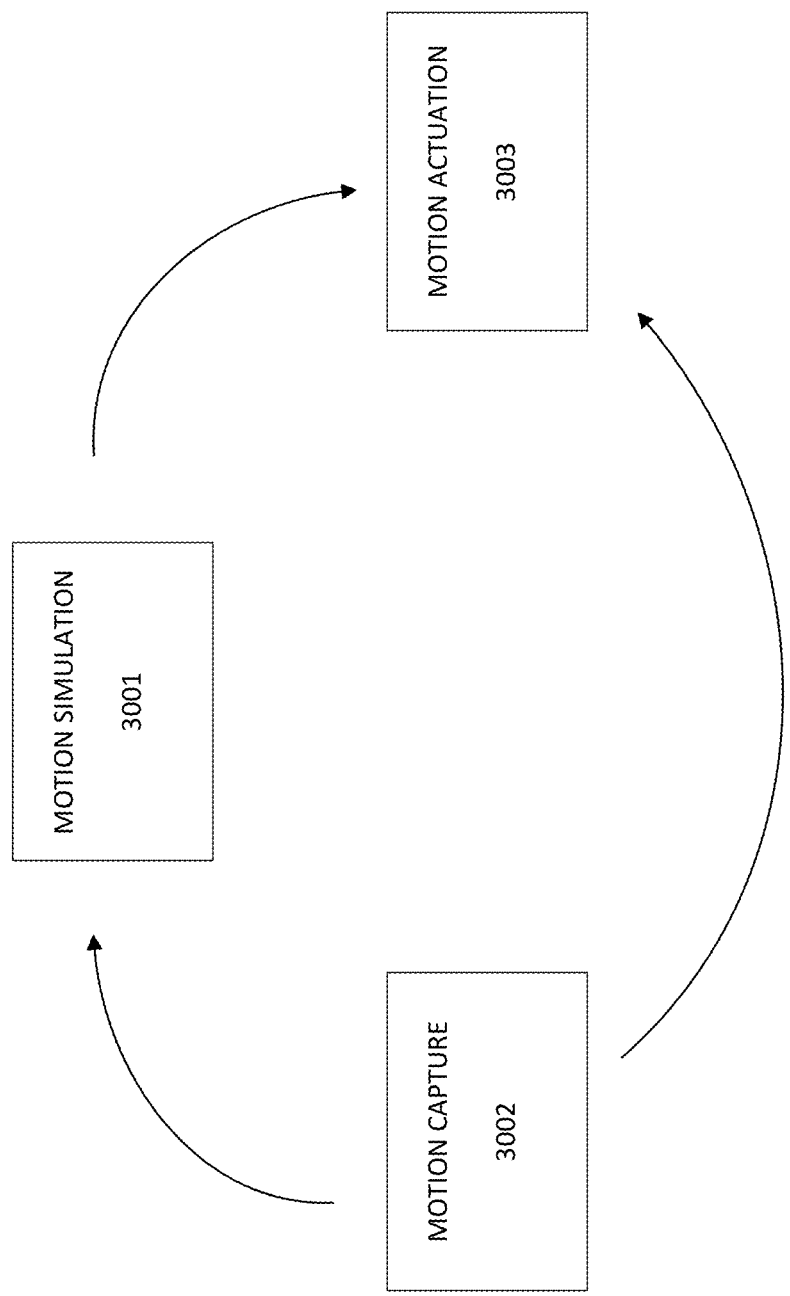
FIG. 7 is a diagram showing a motion system with a motion capture unit, a motion simulation unit and a motion actuation unit.

Additionally and alternatively, the system 1000 can comprise a motion simulating unit 3001 (FIG. 7) that is in communication with a motion capture unit 3002 and a motion actuation unit 3003 of the system 1000. The motion capture unit 3002 comprises a plurality of motion sensors. For example, the motion sensors can be surface electromyography (sEMG) sensors that can be positioned remotely from the system 1000. The signals from the motion sensors are process by the motion simulating unit 3001 which then provides signals to the motion actuation unit 3003. The motion actuation system 3003 can be the motion system 1000 with the plurality of actuators 100. So, the signals from the motion sensors are process by the motion simulating unit 3001 which then provides signals to the central controller of the motion system 1000 to accordingly actuate the actuators 100 to mimic the predetermined motion trajectory that was simulated by the simulating unit 3001. In one implementation the plurality of sensors (sEMG sensors) can be located to a trainer (e.g. a human being). In such implementation, the motion sensors located at a specific parts of the human body can detect the bioelectrical potential generated by muscle cells and the signals can be sent to a simulating unit 3001 to analyze and detect the activity of the wearer's target muscles (and his/her intention). The signals from the simulating unit 3001, and in some implementations signals from the sensors (motion capture unit 3002) can be fed into the motion actuation unit 3003 (e.g. the system's central controller) as input to generate output signals (driving signals) to the actuators 100 of the system 1000 to control the motion (movements) of the system 1000. For example the motion simulating system illustrated in FIG. 7 can be used in applications where the trainer can remotely control the movement of a robotic structure.

Additionally and alternatively, a safety assembly can be provided to protect against potential falls which may occur due to reasons such as collision with objects, slippery surfaces, etc. The safety assembly may comprise a rechargeable polyurethane foam bag, an airbag system or any other system used for protecting fragile structures and mechanisms. The safety assembly is in communication with the controller that can trigger such safety mechanism based on the input it receives from the sensors (IMU sensors).

While particular elements, embodiments and applications of the present disclosure have been shown and described, it will be understood, that the scope of the disclosure is not limited thereto, since modifications can be made by those skilled in the art without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another, or may be combined in various ways. All possible combinations and subcombinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments. Indeed, the novel methods and systems described herein may be embodied in a variety of other forms; furthermore, various omissions, additions, substitutions, equivalents, rearrangements, and changes in the form of the embodiments described herein may be made without departing from the spirit of the inventions described herein.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The example calculations, simulations, results, graphs, values, and parameters of the embodiments described herein are intended to illustrate and not to limit the disclosed embodiments. Other embodiments can be configured and/or operated differently than the illustrative examples described herein.

The invention claimed is:

1. A motion system comprising:
 a plurality of Stewart platform based actuators connected one to each another forming a desired modular configuration, each of the plurality of Stewart platform actuators comprising a plurality of kinematic legs, an upper plate, a base plate and at least one driver in communication with the plurality of kinematic legs, the plurality of the kinematic legs being pivotally connected to the base plate and the upper plate extending therein between, the at least one driver configured to independently drive each of the plurality of kinematic legs to change length and orientation of the legs such that a position of one of the plates moves within six degrees of freedom relative to the other plate;

at least one damper linking element positioned and connecting at least two neighboring actuators; and a central controller having an input unit, a processing unit and an output unit and being in communication with the at least one driver of each of the plurality of actuators to independently control length, orientation and speed of each of the plurality of kinematic legs of each of the plurality of actuators to adjust in real time their position, orientation and motion trajectory.

2. The motion system of claim 1, further comprising a plurality of sensors to measure a position of each of the legs of each of the actuator in real time, the input unit of the central controller receiving an input signal from the plurality of sensors, the processing unit calculating the length, orientation and velocity of each of the plurality of legs of each of the actuators based on the received input signal, and the output unit triggering the at least one driver of each of the actuators to adjust a trajectory of each of the plurality of kinematic legs of each of the actuators in real time.

3. The motion system of claim 2, wherein the plurality of sensors are inertial measurement unit (IMU) sensors.

4. The motion system of claim 3, wherein the plurality of sensors include at least a 3-axial rate gyro.

5. The motion system of claim 1, wherein the input unit of the central controller receive an input signal by an operator and adjusts a trajectory of each of the actuators in real time based on the received input signal.

6. The motion system of claim 1, wherein the linking damper further comprising a driver in communication with the damper and a controller in communication with the driver to control and adjust the stiffness of the damper in real time.

7. The motion system of claim 1, further comprising a reinforcing damper rotatably connected to the upper plate and the base plate of at least one of the actuator, the reinforcing damper having a driver and a controller in communication with the driver to control and adjust the stiffness of such actuator in real-time.

8. The motion system of claim 7, wherein the reinforcing damper is a Magnetorheological (MR) damper.

9. The motion system of claim 1, further comprising a plurality of microcontrollers, each of the plurality of microcontrollers being in communication with the plurality of actuators to control and adjust a position, orientation and a motion trajectory of such actuators, each of the plurality of microcontrollers being in communication with the central controller.

10. The motion system of claim 1, wherein the central controller further comprises a signal conditioning circuit.

11. The motion system of claim 1, further comprising a driver in communication to the damper and the controller, the controller triggering the driver to adjust the stiffness of the motion system.

12. The motion system of claim 1, wherein the damper linking element is a Magnetorheological (MR) damper.

13. The motion system of claim 1, wherein the at least one of the plurality of kinematic legs is a reinforcing Magnetorheological (MR) damper.

14. A motion system comprising:
a plurality of Stewart platform based actuators connected one to each another forming a desired modular configuration, each of the plurality of Stewart platform actuators comprising a plurality of kinematic legs, an upper plate, a base plate and at least one driver in communication with the plurality of kinematic legs, the plurality of the kinematic legs being pivotally connected to the base plate and the upper plate extending therein between, the at least one driver configured to independently drive each of the plurality of kinematic legs to change length and orientation of the legs such that a position of one of the plates moves within six degrees of freedom relative to the other plate;

a reinforcing damper rotatably connected to the upper plate and the base plate of at least one of the actuator to adjust the stiffness of such actuator; and a central controller having an input unit, a processing unit and an output unit and being in communication with the at least one driver of each of the plurality of actuators to independently control length, orientation and speed of each of the plurality of kinematic legs of each of the plurality of actuators to adjust in real time their position, orientation and motion trajectory.

15. The motion system of claim 14, further comprising a plurality of sensors to measure a position of each of the legs of each of the actuator in real time, the input unit of the central controller receiving an input signal from the plurality of sensors, the processing unit calculating the length, orientation and velocity of each of the plurality of legs of each of the actuators based on the received input signal, and the output unit triggering the at least one driver of each of the actuators to adjust a trajectory of each of the plurality of kinematic legs of each of the actuators in real time.

16. The motion system of claim 15, wherein the plurality of sensors are inertial measurement unit (IMU) sensors.

17. The motion system of claim 16, wherein the plurality of sensors include at least a 3-axial rate gyro.

18. The motion system of claim 14, further comprising at least one linking element between and connecting two neighboring actuators.

19. The motion system of claim 18, wherein the linking element is a damper linking element.

20. The motion system of claim 19, wherein the damper linking element is a Magnetorheological (MR) damper.

21. The motion system of claim 19, wherein the damper linking element further comprising a driver in communication with the damper linking element and a controller in communication with the damper driver to control and adjust the stiffness of the damper linking element.

22. The motion system of claim 14, wherein the reinforcing damper having a driver and a controller in communication with the driver of the reinforcing damper to control and adjust the stiffness of the reinforced actuator.

23. The motion system of claim 14, wherein the reinforcing damper is a Magnetorheological (MR) damper.

24. The motion system of claim 14, wherein the at least one of the plurality of kinematic legs is a reinforcing Magnetorheological (MR) damper.

25. The motion system of claim 14, further comprising a plurality of microcontrollers, each of the plurality of microcontrollers being in communication with the plurality of actuators to control and adjust a position, orientation and a motion trajectory of such actuators, each of the plurality of microcontrollers being in communication with the central controller.

26. The motion system of claim 14, wherein the central controller further comprises a signal conditioning circuit.

\* \* \* \* \*